(12) United States Patent
Singleton

(10) Patent No.: US 8,236,287 B2
(45) Date of Patent: Aug. 7, 2012

(54) SUNSCREEN COMPOSITIONS

(75) Inventor: Laura C. Singleton, Los Angeles, CA (US)

(73) Assignee: Neutrogena Corporation, Los Angeles, CA (US)

( * ) Notice: Subject to any disclaimer, the term of this patent is extended or adjusted under 35 U.S.C. 154(b) by 144 days.

(21) Appl. No.: 12/875,163

(22) Filed: Sep. 3, 2010

(65) Prior Publication Data

US 2012/0058192 A1    Mar. 8, 2012

(51) Int. Cl.
*A61Q 17/04*    (2006.01)
*A61K 9/16*    (2006.01)

(52) U.S. Cl. .............................. 424/59; 424/60; 424/493

(58) Field of Classification Search .................... 424/59, 424/60, 493
See application file for complete search history.

(56) References Cited

U.S. PATENT DOCUMENTS

| | | | |
|---|---|---|---|
| 4,551,330 A | 11/1985 | Wagman et al. | |
| 5,118,507 A | 6/1992 | Clement | |
| 5,152,983 A | 10/1992 | Nambudiry et al. | |
| 5,216,033 A | 6/1993 | Pereira et al. | |
| 5,962,018 A | 10/1999 | Curtis et al. | |
| 6,197,281 B1 | 3/2001 | Stewart et al. | |
| 2004/0067206 A1 | 4/2004 | Paspaleeva-Kuhn et al. | |
| 2006/0128883 A1 | 6/2006 | Garrison et al. | |
| 2007/0116696 A1 | 5/2007 | Riley | |
| 2008/0014155 A1 | 1/2008 | Marrs | |
| 2009/0035234 A1* | 2/2009 | Cunningham et al. | 424/59 |
| 2010/0092410 A1* | 4/2010 | Cockerell et al. | 424/59 |
| 2010/0135939 A1* | 6/2010 | Lehmann et al. | 424/60 |
| 2010/0310481 A1 | 12/2010 | Chevalier et al. | |

OTHER PUBLICATIONS

COSMOSURF CE-100 Data Sheet, http://www.surfatech.com/pdfs/MSDS%20Cosmosur%20CE-100.pdf .revised Mar. 27, 2010.*
Chen et al., "Evaluation of Antioxidant and DNA Protection Activities in the Extracts of Leaves of the *Lotus* Plant", *Chia Nan University of Pharmacy & Science Institutional Repository* (Aug. 2009).
COSMOSURf CE-100 Data Sheet, http://www.surfatech.com/pdfs/MSDS%20Cosmosurf%20CE-100.pdf Retrieved Dec. 18, 2011 Section 1.
Kim et al., "Prediction of Interfacial Tension between Oil Mixtures and Water", Journal of Colloid and Interface Science, 241(2):509-513 (Sep. 15, 2001).
Hughes et al., "Novel Methods for Emollient Characterization", Cosmetics and Toiletries Manufacture Worldwide, pp. 19-24 (2006).

* cited by examiner

*Primary Examiner* — Blessing Fubara

(57) ABSTRACT

Sunscreen compositions containing a discontinuous oil phase dispersed in a continuous water phase, at least 10% by weight of an organic UV-filter, a water-insoluble, $C_2$-$C_8$, liquid silicone, a branched fatty acid ester of a polyprotic carboxylic acid; and at least 2% by weight of a mineral particulate having a starch coating applied to the surface thereof.

11 Claims, No Drawings

SUNSCREEN COMPOSITIONS

FIELD OF THE INVENTION

The present invention relates to topical sunscreen compositions having the ability to be successfully applied to wet skin.

BACKGROUND OF THE INVENTION

Conventional sunscreen products generally take the form of UV-filter compounds and/or particulate UV-screening compounds (collectively, "sunscreen actives") that are solubilized, emulsified, or dispersed in a vehicle, which is topically applied to the skin. The sunscreen actives, typically through the aid polymers and other ingredients included in the vehicle, form a thin, protective, and often water-resistant layer on the skin.

The applicants have recognized that, unfortunately, while typical sunscreen products are successful at providing a durable protective barrier when applied to dry skin, such is not typically the result when applied to skin that is damp with sweat or has residual water thereon. In fact, when applied to wet skin, the tendency of conventional sunscreen products is to dilute the sunscreen actives, smear, form an incomplete film, often one that flakes or peels off the skin, and/or takes on a pasty, white appearance. The inventors have found that this undesirable whitening is particularly problematic when the composition itself includes water.

Others have contemplated a solution to applying sunscreen to wet skin by using a water-in-oil emulsifier to "self-emulsify," presumably in the presence of residual water present on the skin. However, the applicants have recognized that severe aesthetic and performance problems still exist in prior art "wet skin" sunscreen products. Accordingly, the applicants have now identified a new composition that provides consistent and pleasant application to wet skin as well as the ability of the resulting film to protect the skin from damaging ultraviolet radiation.

SUMMARY OF THE INVENTION

The present invention relates to sunscreen compositions comprising a discontinuous oil phase dispersed in a continuous water phase, about 10 percent or more by weight of an organic UV-filter, a water-insoluble, low-volatility, $C_2$-$C_8$, liquid silicone, a branched fatty acid ester of a polyprotic carboxylic acid; and about 2 percent or more by weight of a mineral particulate comprising a starch coating applied to the surface thereof.

DETAILED DESCRIPTION OF THE INVENTION

As used herein, "cosmetically acceptable" means suitable for use in contact with tissues (e.g., the skin) without undue toxicity, incompatibility, instability, irritation, allergic response, or the like. All percentages herein are percent by weight based on total concentration of the composition, oil or water phases, or mineral particulate, respectively.

Compositions of the present invention include a discontinuous oil phase and a continuous water phase. As one of ordinary skill in the art would understand, by "discontinuous oil phase," it is meant a physically distinctive aggregation of intimately mixed organic, hydrophobic compounds that are stabilized within a water phase. Compounds that may be included in the oil phase include, for example, organic, UV-filters, liquid silicones, fatty acid esters of polycarboxylic acids, oil-gelling agents, and waxes, among other hydrophobic compounds. The concentration of the oil phase in the composition may be from about 10 percent to about 80 percent, such as from about 20 percent to about 70 percent, such as from about 30 percent to about 60 percent, such as from about 40 percent to about 60 percent.

By "continuous water phase" it is meant a physically distinctive aggregation of water and other optional ingredients that are generally hydrophilic and intimately mixed therewith. Ingredients suitable for use in the water phase include, for example water, dissolved salts such as sodium chloride, water soluble surfactants, water-soluble preservatives and dyes, chelating agents, pH adjusters and buffers (e.g., citric acid, sodium hydroxide, bicarbonate and the like), water-soluble biologically active compounds, glycerin, glycols, and the like. In certain embodiments of the invention, the concentration of water phase in the composition is from 20% to about 90%, such as from about 30% to about 80%, such as from about 35% to about 65%, such as from about 40% to about 65% by weight of the composition. In certain embodiments, the concentration of the water phase is greater than the concentration of the oil phase.

In certain embodiments, the discontinuous oil phase may be substantially homogeneously dispersed in the water phase and may be phase stable. By "phase stable", it is meant that there is no appreciable separation or settling of the oil phase from the water phase after being exposed to 40° C. for two weeks. In certain embodiments, there is no appreciable separation or settling of the oil phase from the water phase after being exposed to 40° C. for six weeks, or in other embodiments after being exposed to 40° C. for three months. In such phase stable compositions, the discontinuous oil phase may be stabilized within the continuous water phase such that the discrete oil phase is present such that the majority of the particles have a particle size that is from about 0.2 microns to about 10 microns, more preferably from about 0.5 microns to about 5 microns, most preferably from about 0.75 microns to about 5 microns. In other embodiments, compositions may be such that the oil phase may be dispersed within the water phase with light to moderate agitation prior to use.

Compositions of the present invention include an organic UV-filter. Organic UV filters that are useful in the present invention are cosmetically-acceptable compounds that absorb radiation in the UV range and are generally soluble in one or more organic hydrocarbon solvents. The organic, UV-filter absorbs radiation in some portion of the ultraviolet spectrum (290 nm-400 nm), and may have an extinction coefficient of at least about 1000 $mol^{-1}$ $cm^{-1}$, for example greater than 10,000 or 100,000 or 1,000,000 $mol^{-1}$ $cm^{-1}$, for at least one wavelength within the above-defined ultraviolet spectrum.

Examples of organic UV filters include, without limitation, 3-benzylidene camphor, specifically 3-benzylidene norcamphor and derivatives thereof, e.g. 3-(4-methylbenzylidene) camphor; 4-aminobenzoic acid derivatives, specifically 4-(dimethylamino)benzoic acid-2-ethylhexyl esters, 4-(dimethylamino)benzoic acid-2-octyl esters and 4-(dimethylamino)benzoic acid amylesters; esters of cinnamonic acid, in particular 4-methoxycinnamonic acid-2-ethylhexylester, 4-methoxycinnamonicacid propylester, 4-methoxycinnamonic acid isoamyl ester, 2-cyano-3,3-phenylcinnamonic acid-2-ethylhexyl ester (octocrylene); esters of salicylic acid, i.e., salicylic acid-2-ethylhexylester, salicylic acid-4-isopropylbenzyl ester, salicylic acid homomethyl ester; derivatives of benzophenones, in particular 2-hydroxy-4-methoxybenzophenone, 2-hydroxy-4-methoxy-4'-methylbenzophenone, 2,2'-dihydroxy-4-methoxybenzophenone; esters of benzalmalonic acid, in particular 4-methoxybenzmalonic acid di-2-ethylhexyl ester; triazine derivatives, for example 2, 4,6-trianilino-(p-carbo-2'-ethyl-1'-hexyloxy)-1,3,5-triazine and octyltriazone; or benzoic acid, 4,4'-[[6-[[[(1,1-dimethylethyl)amino]carbonyl]phenyl]amino]-1,3,5-triazine-2,4-diyl]diimino]bis-, bis(2-ethylhexyl) ester (UVASORB HEB); propane-1,3-diones, for example, 1-(4-tert.butylphenyl)-3-(4'-methoxyphenyl) propane-1,3-dione; ketotricyclo (5.2.1.0) decane derivatives; derivatives of benzoylmethane, for example, 1-(4'-tert.butylphenyl)-3-(4'-methoxyphenyl) propane-1,3-dione, 4-tert-butyl-4'-methoxydibenzoyl-methane (PARSOL 1789), 1-phenyl-3-(4'-isopropylphenyl)-propane-1,3-dione, derivatives of benzoic acid 2-(4-diethylamino-2-hydroxybenzoyl)-benzoic acid hexylester (UVINUL A+), or 1H-benzimidazole-4,6-disulfonic acid, 2,2'-(1,4-phenylene)bis-, disodium salt (NEO HELOPAN AP); and benzotriazoles, in particular the benzotriazole derivative known as 2,2'-methylene-bis-(6-(2H-benzotriazole-2-yl)-4-(1,1,3,3-tetramethylbutyl)-phenol) [INCI: Bisoctyltriazol], which is commercially available under the tradename TINOSORB M from CIBA Chemicals. Another useful benzotriazole derivative is 2-(2H-benzotriazole-2-yl)-4-methyl-6-[2-methyl-3-[1,3,3,3-tetramethyl-1-[(trimethylsilyl)oxy]disiloxanyl]propyl]-phenol (CAS-No.: 155633-54-8), also identified by the INCI name drometrizole trisiloxane and available from Chimex under the tradename MEXORYL XL. Also suitable are asymmetrical6ly substituted triazine derivatives, and 2,4-bis-{[4-(2-ethyl-hexyloxy)-2-hydroxy]-phenyl}-6-(4-methoxyphenyl)-1,3,5-triazine (INCI: anisotriazine) that is commercially available under the tradename TINOSORB S from CIBA.

In one embodiment, the organic UV-filter is selected from the group consisting of octocrylene, a benzotriazole, anisotriazine, an ester of salicylic acid, an ester of cinnamic acid and a derivative of a benzoylmethane.

The organic, UV-filter is present in the composition in a concentration that is about 10% or more, such as from about 10% to about 40%, such as from about 10% to about 35%, such as from about 15% to about 35%, e.g., from about 20% to about 35% by weight.

As one skilled in the art will readily appreciate, the term "organic UV filter" does not include ultraviolet-screening particles, ("UV-screening particles") typically used at least in part to scatter ultraviolet radiation. Examples include inorganic oxides including titanium dioxide, zinc oxide; iron oxides, silicone oxides; or other metal (e.g., transition metal, such as crystalline transition metal) oxides. UV-screening particles are typically solid particles having a dimension (e.g., a diameter) from about 0.1 micron to about 10 microns. While in certain embodiments of the invention, UV-screening particles may optionally be included in compositions of the present invention, they are excluded in certain other embodiments. For those embodiments in which UV-screening particles are included, the concentration of the UV-screening particles in the composition may be from about 0.1% to about 10%, such as from about 0.5% to about 5%, such as from about 0.5% to about 2%.

Compositions of the present invention include a water-insoluble, low-volatility, $C_2$-$C_8$, liquid silicone. By "low-volatility" it is meant compounds that have a flash point above about 105° C., such as above about 150° C., such as above about 200° C. By liquid silicone, it is meant, a compound having at least one siloxane (Si—O—Si linkage) having a melting point below 25° C. The liquid silicone is, in certain embodiments, insoluble in water, and, in certain embodiments, soluble in isopropanol. The liquid silicone may have a structure that includes one or multiple units of:

—[CH$_3$—SiO—C$_n$H$_{2n}$—CH$_3$]— where n is from 2-8, such as from 2-4. A particularly suitable example is the compound in which n=2, available as SILWAX D02 (INCI: ethyl methicone) from Siltech of Dacula, Ga.

The water-insoluble, low-volatility, $C_2$-$C_8$, liquid silicone generally functions to provide plasticity to the film that is created on the skin, and to prevent whitening (e.g., by increasing the refractive index of the resulting film) that might otherwise occur when the composition contacts water present on the skin. The concentration of non-volatile liquid silicone present in the composition may be from about 0.5% to about 10%, or from about 1% to about 6%, or from about 2% to about 4%.

Compositions of the present invention include a branched fatty acid ester of a polyprotic carboxylic acid ("BFEPCA"). The branched fatty acid ester of a polyprotic carboxylic acid has a melting point below 25° C., is water-insoluble and may be soluble in isopropanol. In a notable embodiment, the BFEPCA is a reaction product of a polyprotic acid with a $C_{10}$-$C_{30}$ fatty acid, such as a $C_{12}$-$C_{22}$ fatty acid. The fatty acid may be branched. The polyprotic acid may be selected from the group consisting of citric acid, ascorbic acid, phosphoric acid and sulphuric acid. In one embodiment, the polyprotic acid is citric acid or ascorbic acid. Citric acid is particularly notable.

For example, the BFEPCA may have five or more ester groups per molecule. One suitable example of a BFEPCA is an octyldodecyl citrate polyester which is commercially available as COSMOSURF CE-100 from SurfaTechCorporation/Siltech Corporation of Dacula, Ga.

The PFECPA assists the ability of the composition to exclude water during formation of the film, yet also serves to prevent peeling in the film and resist degradation from water after the film forms.

The concentration of PFECPA present in the composition may be from about 2% to about 40%, or from about 4% to about 25%, or from about 8% to about 18%. The PFEPCA and the liquid silicone are, in certain embodiments, present in a PFEPCA to liquid silicone ratio that is from about 1.5 to about 8, such as from about 2 to about 4.

Compositions of the present invention include a mineral particulate at least partially coated with a starch. By "particulate" it is meant a finely divided solid that is generally insoluble in water, such as one having an average particle size in a range from about 0.1 microns to about 20 microns. The mineral particulate comprises a mineral portion, such as one including any of various silicas, oxides and/or aluminosilicates; and a coating portion that is applied to the surface of the mineral so as to at least partially coat the mineral portion. The coating may be continuous and cover substantially all of the surface of the mineral portion, or may be discontinuous and cover a substantial portion, but not all of the surface of the mineral portion. The coating portion includes a starch.

The starch may be derived from such plants as corn, wheat, rice, tapioca, potato, sago, and the like, including either the waxy versions of such starches (containing less than 5% amylose), high amylase starches (containing more than 40% amylose), those with a modified chain length, and/or combinations thereof. In certain preferred embodiments, the starch is rice starch.

The mineral portion may be present in a weight percentage of the mineral particulate that is from about 80% to about 98%, such as from about 80% to about 97%, such as from about 85% to about 96%. The coating portion may be present in a weight percentage of the mineral particulate that is from about 2% to about 20%, such as from about 3% to about 20%, such as from about 4% to about 15%.

The mineral particulate, in certain embodiments, has mineral oil absorption capacity of about 20 ml/100 g or greater, such as about 100 ml/100 g or greater, such as about 200 ml/100 g or greater. Mineral oil absorption capacity is determined by placing 3-5 grams of test sample on a glass plate and adding mineral oil one drop at a time and mixing with a spatula. The end point is indicated when the sample produces a very stiff paste which does not break or separate. The paste should be able be rolled with the spatula without separation. Testing is done in triplicate.

The mineral particulate may be prepared by any of various means known to those skilled in the art. Suitable methods include coating mineral particles with a starch by spraying the starch onto the mineral particles and subsequently drying.

In one exemplary process, water and rice starch are mixed together and heated for a time sufficient to gelatinize the starch. This gelatinized starch mixture is sprayed at high pressure onto porous spherical silica particles that have a diameter in the range of from about 1 micron to about 10 microns. During the spraying process, the silica is mixed in a high intensity, hi speed mixer to ensure homogeneous coating. The mixture of silica and gelatinized starch is then dried under vacuum for a period of time sufficient to remove the water. The relative proportions of silica and starch coated thereon are selected to achieve a weight ratio of silica to starch of about 95:5.

Since the mineral particulate is insoluble in either the oil phase or the water phase, the particulate generally exists in the composition as a discrete dispersed phase, i.e., not part of either oil phase or water phase.

The amount of mineral particulate in the composition is about 2% or more by weight. In certain embodiments the mineral particulate is present in a concentration of about 4% or more, such as from about 4% to about 10%, or from about 4% to about 8%.

Compositions of the present invention may include an oil-gelling agent. By "oil-gelling agent," it is meant a compound that is capable of forming a gel with mineral oil or dimethicone. In particular, when the oil-gelling agent is mixed with mineral oil or dimethicone to a concentration of oil-gelling agent that is between about 0.25% to 2.0% by weight, the resulting mixture has a yield stress of at least about 5 pascals (Pa), such as at least about 10 Pa, such as from about 10 Pa to about 1100 Pa.

Suitable oil-gelling agents include glycerol esters of various fatty acids, e.g. glycerol esters of fatty acids having a carbon chain length of at least $C_{16}$. A suitable example is a mixture of mono, di, and triglycerides of behenic acid ($C_{22}$) sold under the trade name COMPRITOL 888 from Gattefosse of France.

Other suitable oil-gelling agents include copolymers of siloxanes and monomers including hydrophilic moieties, such as copolymers of siloxanes and monomers having alkoxy moieties. Suitable examples include materials sometimes classified as water-in-silicone emulsifiers. A suitable example is PEG/PPG-19/19 dimethicone, which is sold in cyclopentasiloxane solvent as Dow Corning BY-11030 available from Dow Corning of Midland, Mich.

Other suitable oil-gelling agents include copolymers of such monomers as ethylene, propylene, butylene, and/or styrene, e.g., terpolymers of ethylene, propylene, and styrene and terpolymers of butylenes, ethylene, and styrene. Such terpolymers are sold under the trade name VERSAGEL F-1000 from Penreceo of Los Angeles, Calif.

Other particularly suitable oil-gelling agents include ethylcellulose, an ethyl ether of cellulose comprising a long-chain polymer consisting of anhydroglucose units joined together by acetal linkages. A suitable form of ethylcellulose is available as a mixture with cocoate mono and di-esters of butylene glycol and isostearyl alcohol (fatty alcohol). This mixture is sold as "EMULFREE CBG available from Gattefosse of Paris, France.

Compositions of the present invention may include a film forming polymer to enhance film formation and provide some water resistance. By "film-forming polymer," it is meant a polymer that when dissolved in the composition, permits a continuous or semi-continuous film to be formed when the composition is spread onto, e.g., smooth glass, and the liquid vehicle is allowed to evaporate. As such, the polymer should dry on the glass in a manner in which over the area which it is spread should be predominantly continuous, rather than forming a plurality of discrete, island-like structures. Generally, the films formed by applying compositions on the skin according to embodiments of the invention described herein, are less than, on average, about 100 microns in thickness, such as less than about 50 microns.

Suitable film-forming polymers include natural polymers such as polysaccharides or proteins and synthetic polymers such as polyesters, polyacrylics, polyurethanes, vinyl polymers, polysulfonates, polyureas, polyoxazolines, and the like. Specific examples of film-forming polymers include, for example, acrylic homopolymers or copolymers with hydrophobic groups such as acrylate/ocylacrylamide copolymers including DERMACRYL 79 available from Akzo Chemical of Bridgewater, N.J.; dimethicone/acrylates dimethicone copolymer available as X-22-8247D from Shin-Etsu of Japan; hydrogenated dimer dilinoleyl/dimethylcarbonate copolymer, available from Cognis Corporation of Ambler, Pa. as COSMEDIA DC; copolymer of vinylpyrrolidone and a long-chain a-olefin, such as those commercially available from ISP Specialty Chemicals of Wayne, N.J. as GANEX V220; vinylpyrrolidone/tricontanyl copolymers available as GANEX WP660 also from ISP; water-dispersible polyesters, including sulfopolyesters such those commercially available from Eastman Chemical as EASTMAN AQ 38S. In certain embodiments, the film-forming polymer is water insoluble, but is rendered soluble upon exposure to alkalinity in order to facilitate removal from the skin upon washing with soap.

The amount of film-forming polymer present in the composition may be from about 0.25% to about 15%, or from about 0.5% to about 10%, or from about 1% to about 3%.

In certain embodiments, the composition includes a wax. By wax, it is meant one or more hydrophobic compounds that have a melting point that is in the range from 30° C. to 120° C., such as in the range from 45° C. to 100° C. In one embodiment, the wax component includes a wax compound having a melting point from about 75° C. to 100° C.

By "additional hydrophobic compound," it is meant a compound that includes a hydrophobic moiety that meets one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is not amphiphilic and, and such, does not include hydrophilic moieties, such as anionic, cationic, zwitterionic, or nonionic group, that is polar, including sulfate, sulfonate, carboxylate, phosphate, phosphonates, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the hydrophobic compound does not include hydroxyl moieties.

Suitable waxes include any of various hydrocarbons (straight or branched chain alkanes or alkenes, ketone, diketone, primary or secondary alcohols, aldehydes, sterol esters, alkanoic acids, turpenes, monoesters), such as those having a carbon chain length ranging from $C_{12}$-$C_{38}$. Also suitable are diesters or other branched esters. In one embodiment, the compound is an ester of an alcohol (glycerol or other than glycerol) and a $C_{18}$ or greater fatty acid.

Non-limiting examples include any of various natural waxes including lotus wax (e.g., Nelumbo Nucifera Floral Wax available from Deveraux Specialties, Silmar, Calif.); beeswax (e.g., White Beeswax SP-422P available from Strahl and Pitsch of West Babylon, N.Y.), insect waxes, sperm whale oil, lanolin, vegetable waxes such as canauba wax, jojoba oil, candelilla wax; mineral waxes such as paraffin wax; and synthetic waxes such as cetyl palmitate, lauryl palmitate, cetostearyl stearate, and polyethylene wax (e.g., PERFORMALENE 400, having a molecular weight of 450 and a melting point of 84° C., available from New Phase Technologies of Sugar Land, Tex.); and silicone waxes such as $C_{30\text{-}45}$ Alkyl Methicone and $C_{30\text{-}45}$ Olefin (e.g., Dow Corning AMS-C30, having a melting point of 70° C., available from Dow Corning of Midland, Mich.). In certain embodiments, the wax component includes a high melting point ester of glycerol such as glycerol monostearate.

The amount of wax may be present in the composition from about 0.1% to about 5%, or from about 0.1% to about 2%, or from about 0.1% to about 1%.

Compositions of the present invention may include an alkyl-modified silicone polymer. The dispersed alkyl-modified silicone polymer may be insoluble in isopropanol as well insoluble in water. The alkyl-modified silicone polymer generally includes a $C_8$-$C_{30}$ linear or cyclic, saturated or unsaturated alkyl group, such as a $C_{12}$-$C_{22}$ alkyl group.

The alkyl-modified silicone generally serves to reduce surface tension, improve water exclusion and reduce whitening. An example of a suitable alkyl-modified silicone polymer that disperses well in solvents such as isopropanol include copolymers of cetyl dimethicone and bis-vinyl dimethicone, such as SILWAX CR-5016, commercially available from SilTech of Dacula, Ga. For embodiments in which the alkyl-modified silicone polymer is insoluble in either the oil phase or the water phase, the alkyl-modified silicone polymer may exist in the composition as a discrete dispersed phase, i.e., not part of either oil phase or water phase.

The amount of dispersed alkyl-modified silicone polymer may present in the composition may be from about 0.1% to about 1%, or from about 0.1% to about 0.5%, or from about 0.1% to about 0.25%.

Any of various other cosmetically-acceptable ingredients may be included in the composition in amounts so as to not counter the effects of the various other ingredients. For example, ingredients such as oils (including emollient esters and triglycerides) of vegetable, animal, or mineral origin, fragrances, dyes, preservatives, skin benefit agents, photostabilizers, anti-oxidants, water-phase gelling agents (such as gylceryl disterate or hydrophobically modified acrylic or other thickening polymers), neutralizing agents (such as triethanolamine, sodium hydroxide, and the like).

The other ingredients may be included, in, for example total concentrations that are less than about 10%, such as less than about 5%, such as less than about 2%, e.g., less than about 1%.

EXAMPLES

The following non-limiting examples further illustrate the claimed invention:

Example I

Preparation of Inventive Examples

The following inventive compositions were prepared:

| Trade Name | CTFA Name | Ex. 1 | Ex. 2 | Ex. 3 | Ex. 4 | Ex. 5 |
|---|---|---|---|---|---|---|
| Water | Water | 45.25 | 47.48 | 43.46 | 55.22 | 51.50 |
| PEMULEN TR-2 | Acrylates/$C_{10\text{-}30}$ Alkyl Acrylate Crosspolymer | 0.25 | 0.25 | 0.25 | 0.25 | 0.3 |
| | Disodium EDTA | 0.2 | 0.1 | 0.1 | 0.2 | 0.2 |
| | Dipotassium Glycyrrhizate | 0.1 | 0.1 | 0.1 | 0.1 | 0.1 |
| | Chlorphenesin | 0.2 | 0.2 | 0.2 | 0.2 | 0.2 |
| | Phenoxyethanol | 0.5 | | | 0.5 | 0.5 |
| Uvinul M40 (BASF) | Oxybenzone; Benzophenone-3/ | 6.00 | 5.00 | 5.00 | 5.00 | 5.00 |
| Octisalate | Octyl Salicylate | 5.00 | 5.00 | 5.00 | 5.00 | 5.00 |
| Avobenzone | Neo Heliopan 357 (Symrise) | 3.00 | 3.00 | 3.00 | 3.00 | 3.00 |
| Neo Heliopan 303 (Symrise) | Octocrylene | 10 | 10 | 10 | 4 | 4 |
| | Homosalate | 7.0 | 4.0 | 7.0 | 4.0 | 4.0 |
| CorapanTQ (CP Hall) | Diethylhexl 2,6 Naphtalate | 0.1 | 0.10 | 0.10 | 0.10 | 0.1 |
| Lotus Wax (Deveraux) | | 0.5 | 0.50 | 0.50 | 0.50 | 0.50 |
| Beeswax | | 2.0 | 2.0 | 2.0 | 2.0 | 0.3 |
| X-22-8247D (ShinEtsu) | Dimethicone (and) Acrylates/Dimethicone Copolymer | 1.5 | 1.50 | 1.50 | 1.50 | 1.75 |
| Sesnsiva | Ethylhexylglycerin | 1.0 | 1.0 | 1.0 | 1.0 | 1.0 |
| Lexguard O (Inolex) | Caprylyl glycol | 0.5 | 0.5 | 0.5 | 0.5 | 0.5 |
| Arlacel 165 VEG | Glyceryl stearate/PEG-100 stearate | 1.9 | 1.9 | 1.9 | 1.9 | 1.9 |
| Amphisol K | Potassium cetyl phosphate | 0.9 | 1.0 | 1.0 | 1.0 | |
| Compritol 888 (Gattefosse) | Glyceryl (mono, di, tri) beheneate | | | | | 1.0 |
| Octyldodecyl Citrate Crosspolymer (and) Ethyl Methicone (and) Cetyl Dimethicone/bis | Blend | 5.0 | 3.5 | 5.0 | 3.0 | 3.0 |

-continued

| Trade Name | CTFA Name | Ex. 1 | Ex. 2 | Ex. 3 | Ex. 4 | Ex. 5 |
|---|---|---|---|---|---|---|
| Vinyl Dimethicone Crosspolymer [1] | | | | | | |
| | BHT | 0.7 | 0.7 | 0.7 | 0.7 | 0.7 |
| Sunspheres | Styrene/acrylate copolymer | 2.0 | 1.0 | | | |
| Water (Neutralization) | | 1.5 | 1.5 | 1.5 | 1.5 | 6.5 |
| Triethanolamine | | 0.3 | 0.25 | 0.27 | 0.16 | 0.45 |
| Water | | | 2.4 | 2.4 | | |
| Cosmocil CQ | Propylamidopropyl guanide | | 0.4 | 0.4 | | |
| Reosol AVH | Ethylhexyl stearate; trideceth-6 | 0.1 | 0.1 | 0.5 | 0.15 | |
| | Benzyl alcohol | 1.0 | 1.0 | 1.0 | 1.0 | 1.0 |
| Fragrance | | 0.13 | 0.15 | 0.15 | 0.15 | 0.3 |
| Mineral Particulate | Silica, coated with rice starch | 4.0 | 6.0 | 6.0 | 8.0 | 8.0 |
| TOTAL | | 100 | 100 | 100 | 100 | 100 |

[1] A blend of 79.8% of octyldodecyl citrate polyester (COSMOSURF CE-100), 20% ethyl methicone (SILWAX D02), and 0.2% of a copolymer of cetyl dimethicone and bis-vinyl dimethicone (SILWAX CR-5016), each available from SilTech.

Examples were prepared by first preparing a preliminary water phase mixture by charging a vessel with the water, PEMULEN TR-2, disodium EDTA, dipotassium glycyrrizate, and chlorphenesin, heating the mixture to 80° C. and mixing until homogeneous. Phenoxyethanol (gelling agent) was then added in the case of Examples 1, 4 and 5 and the mixture again was mixed until homogeneous. In a secondary container an oil phase mixture was prepared by blending the organic UV filters and the other ingredients listed in Table 1, up to and including Sunspheres. The water phase mixture and oil phase mixture was blended for 5 minutes and then homogenized for 3 minutes to form a preliminary emulsion. The preliminary emulsion was then neutralized by cooling to 65° C., adding water and triethanolamine and then mixing until uniform. The neutralized emulsion was allowed to cool to 40° C. and benzyl alcohol and fragrance were added. The mineral particulate was then added slowly with mixing until cooled to 30° C.-32° C. This was homogenized for an additional 1 minute and the balance of any water added. In the case of Example 5, 6.5% of the total water present in the formulation was withheld from the initial charging of the vessel and was added after emulsification.

The Examples were evaluated for stability at 40° C. and adverse whitening on the skin. Stability, an accelerated measure of predicted shelf life, was evaluated by placing the compositions at 40° C. and then observing for any appreciable syneresis, e.g. an appreciable amount of oil phase (liquid) visible at the top of the emulsified composition. Three months stability at 40° C. is equivalent in general to 3 years shelf life of the product, while two months at 40° C. is equivalent in general to 2 years shelf life.

Whitening on the skin was evaluated by immersing the arm of a human subject in water for approximately 1-2 minutes, then applying compositions of the invention to the wet area of the arm and rubbing the compositions into the skin. The compositions were applied in amounts generally effective to provide a continuous film to the skin area, i.e. about 4 grams for the entire male arm or about 3 grams for the entire female arm, typically about 0.5 g/15 cm2 on the same arm.

Example 1 exhibited only a minimal acceptable amount of whitening when applied to the skin and was stable phase stable for 3 months at 40° C. Example 5 showed no discernible whitening on the skin and was stable for 3 months at 40° C. Examples 2 and 4 showed minimal, but acceptable, whitening on the skin and were stable for 2 weeks at 40° C. Example 3 showed no discernible whitening on the skin.

The preceding results suggest that compositions according to the invention are surprisingly capable of providing little to no whitening when applied to wet skin. The preceding results also suggest that varying degrees of stability may be achieved, depending on the particular formulation, by, for example, (a) including an oil gelling agent (such as COMPRITOL), or (b) adding at least 5% (as a percent of entire composition) of the water after emulsification, but before the mineral particulate. For high levels of mineral particulate at least partially coated with starch, by including the oil gelling agent, including higher levels of water, and/or by following the process step of withholding at least 5% water until after emulsification, but before the mineral particulate, stability is enhanced. Once having the benefit of the disclosure herein, one skilled in the art will readily appreciate various factors and steps in order to adjust stability of such compositions.

Example 2

SPF

Examples 1 and 5 were tested for sun protection factor (SPF) using a conventional in-vivo static SPF test method in accordance with the "Sunscreen Drug Products for Over-The-Counter Human Use; Final Monograph" issued by the Food and Drug Administration, May 21, 1999, Federal Register Volume 64, Number 98, 27666-27693. See p 2-3. The test included measuring SPF on dry skin both before and after submersion of the skin in water for a total of 80 minutes. Example 1 exhibited SPF values on dry skin of 92.5 before submersion and 91.85 after submersion. Example 5 exhibited SPF values on dry skin of 55.2 before submersion and 55.0 after submersion.

The same composition was tested using the same method, except that the compositions were applied to wet skin after submersion. The compositions exhibited SPF values of 86.66 and 47.8 respectively, when applied to wet skin after water immersion. These results surprisingly show that the inventive compositions lost only a small fraction of their SPF values when applied to wet skin as compared with when applied to dry skin.

The invention claimed is:
1. A composition, comprising:
a continuous water phase,
a discontinuous oil phase dispersed in said continuous water phase,
about 10 percent or more by weight of an organic UV-filter,
a water-insoluble, $C_2$-$C_8$, liquid silicone,
a branched fatty acid ester of a polyprotic carboxylic acid; and
about 2 percent or more by weight of a mineral particulate, said mineral particulate comprising a mineral portion and a starch coating portion applied to the surface of said mineral portion so as to at least partially coat the mineral portion.
2. The composition of claim 1, wherein said mineral portion comprises silica.

3. The composition of claim 1, wherein said mineral particulate comprises from about 80 percent to about 98 percent by weight of said mineral portion and from about 2 percent to about 20 percent by weight of said starch coating portion.

4. The composition of claim 1 comprising from about 4 percent to about 10 percent by weight of said mineral particulate.

5. The composition of claim 1, wherein said branched fatty acid ester of a polyprotic carboxylic acid comprises an octyldodecyl citrate polyester.

6. The composition of claim 1, wherein said water-insoluble, $C_2$-$C_8$ liquid silicone comprises ethyl methicone.

7. The composition of claim 1, wherein said mineral particulate has a mineral oil absorption capacity of about 20 ml/100 g or greater.

8. The composition of claim 1, wherein said organic UV-filter is selected from the group consisting of octocrylene, a benzotriazole, anisotriazine, an ester of salicylic acid, an ester of cinnamic acid, 1-(4'-tert.butylphenyl)-3-(4'-methoxyphenyl)propane-1, 3-dione, 4-tert-butyl-4'-methoxydibenzoylmethane and 1-phenyl-3-(4'-isopropylphenyl)-propane-1, 3-dione.

9. The composition of claim 4 wherein said mineral particulate comprises a silica having a rice starch applied to the coating thereof, and wherein said composition further comprises a gelling agent.

10. The composition of claim 9 having a stability of 3 months at 40° C.

11. The composition of claim 1 having a stability of 2 weeks at 40° C.

* * * * *